US008062277B2

(12) United States Patent
Fleming

(10) Patent No.: US 8,062,277 B2
(45) Date of Patent: Nov. 22, 2011

(54) ANAL HYGIENIC PAD AND METHOD OF USE

(76) Inventor: William H. Fleming, Tualatin, OR (US)

( * ) Notice: Subject to any disclaimer, the term of this patent is extended or adjusted under 35 U.S.C. 154(b) by 133 days.

(21) Appl. No.: 12/418,167

(22) Filed: Apr. 3, 2009

(65) Prior Publication Data

US 2009/0247972 A1   Oct. 1, 2009

Related U.S. Application Data

(63) Continuation of application No. 10/781,043, filed on Feb. 17, 2004, now abandoned.

(51) Int. Cl.
*A61F 13/15* (2006.01)
(52) U.S. Cl. ....... 604/385.17; 604/385.18; 604/385.101; 604/385.01; 604/359; 604/360; 604/379; 604/380
(58) Field of Classification Search ............. 604/385.17, 604/385.101, 385.18, 385.01, 359, 360, 364, 604/379, 380
See application file for complete search history.

(56) References Cited

U.S. PATENT DOCUMENTS

| | | | |
|---|---|---|---|
| 2,742,042 A | 4/1956 | Flanders |
| 3,712,300 A | 1/1973 | Davidowitz |
| 3,905,372 A | 9/1975 | Denkinger |
| 3,983,873 A | 10/1976 | Hirschman |
| 4,445,899 A | 5/1984 | Bond |
| 4,484,919 A | 11/1984 | Sohn et al. |
| 4,702,237 A | 10/1987 | Gianopoulos et al. |
| 4,804,380 A | 2/1989 | Lassen et al. |
| 4,880,417 A | 11/1989 | Yabrov et al. |
| 4,920,045 A | 4/1990 | Okuda et al. |
| 4,932,397 A | 6/1990 | McFaul, Sr. |
| 5,004,636 A | 4/1991 | Parris |
| 5,073,365 A | 12/1991 | Katz et al. |
| 5,074,855 A | 12/1991 | Rosenbluth et al. |
| 5,211,641 A | 5/1993 | Roos et al. |
| 5,275,591 A | 1/1994 | Mavinkurve |
| 5,336,208 A | 8/1994 | Rosenbluth et al. |
| 5,520,675 A | 5/1996 | Knox-Sigh |
| 5,665,081 A | 9/1997 | Grosse |
| 5,669,902 A | 9/1997 | Sivilich |
| 5,695,484 A | 12/1997 | Cox |
| 5,840,584 A | 11/1998 | Waldenburg |
| 5,968,026 A | 10/1999 | Osborn, III et al. |
| 6,007,498 A | 12/1999 | Buck et al. |
| 6,319,238 B1 | 11/2001 | Sartorio et al. |

(Continued)

FOREIGN PATENT DOCUMENTS

EP       0 531 714       8/1992

(Continued)

*Primary Examiner* — Jacqueline F. Stephens
(74) *Attorney, Agent, or Firm* — Klarquist Sparkman, LLP

(57) ABSTRACT

A method is disclosed for absorbing anal leakage, such as fecal material, blood or flatulence. The method includes positioning an intergluteal absorbent pad external to the anal orifice of a subject such that the pad is retained between the buttocks, and any discharge from the anus is absorbed by the absorbent material of the pad. The pad can have a variety of shapes, including major and minor portions that are portions of spheres or ellipsoids, or which are elongated and have cross-sections that are circular or ellipsoid. The smaller minor portion of the pad is positioned against the anal orifice to minimize pressure exerted in this sensitive area, while the larger major portion is retained in the less sensitive intergluteal space. Insertion and retention of the pad adjacent to the anus helps alleviate symptoms of the hemorrhoids, absorbs leakage, and can also be used as a reservoir to administer medication.

39 Claims, 5 Drawing Sheets

U.S. PATENT DOCUMENTS 6,811,549 B2  11/2004  Fleming
6,967,025 B2  11/2005  Di Cintio et al.

FOREIGN PATENT DOCUMENTS

| | | |
|---|---|---|
| EP | 0 311 344 | 1/1995 |
| EP | 0 591 159 | 7/1996 |
| WO | WO 97/07763 | 3/1997 |
| WO | WO 97/07764 | 3/1997 |
| WO | WO 97/17908 | 5/1997 |
| WO | WO 97/43987 | 11/1997 |
| WO | WO 99/25282 | 5/1999 |
| WO | WO 99/37261 | 7/1999 |
| WO | WO 2004/73757 | 9/2004 |

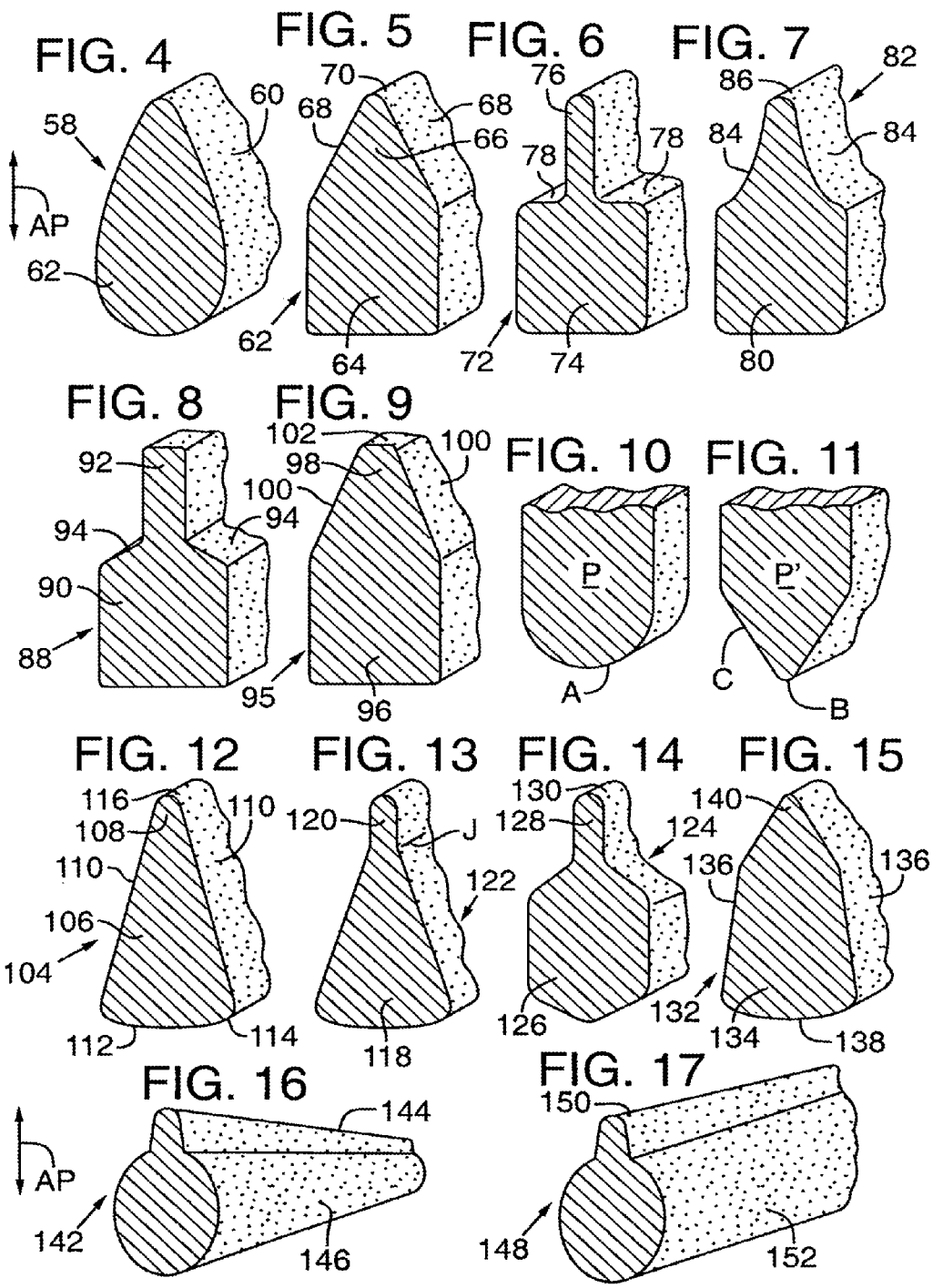

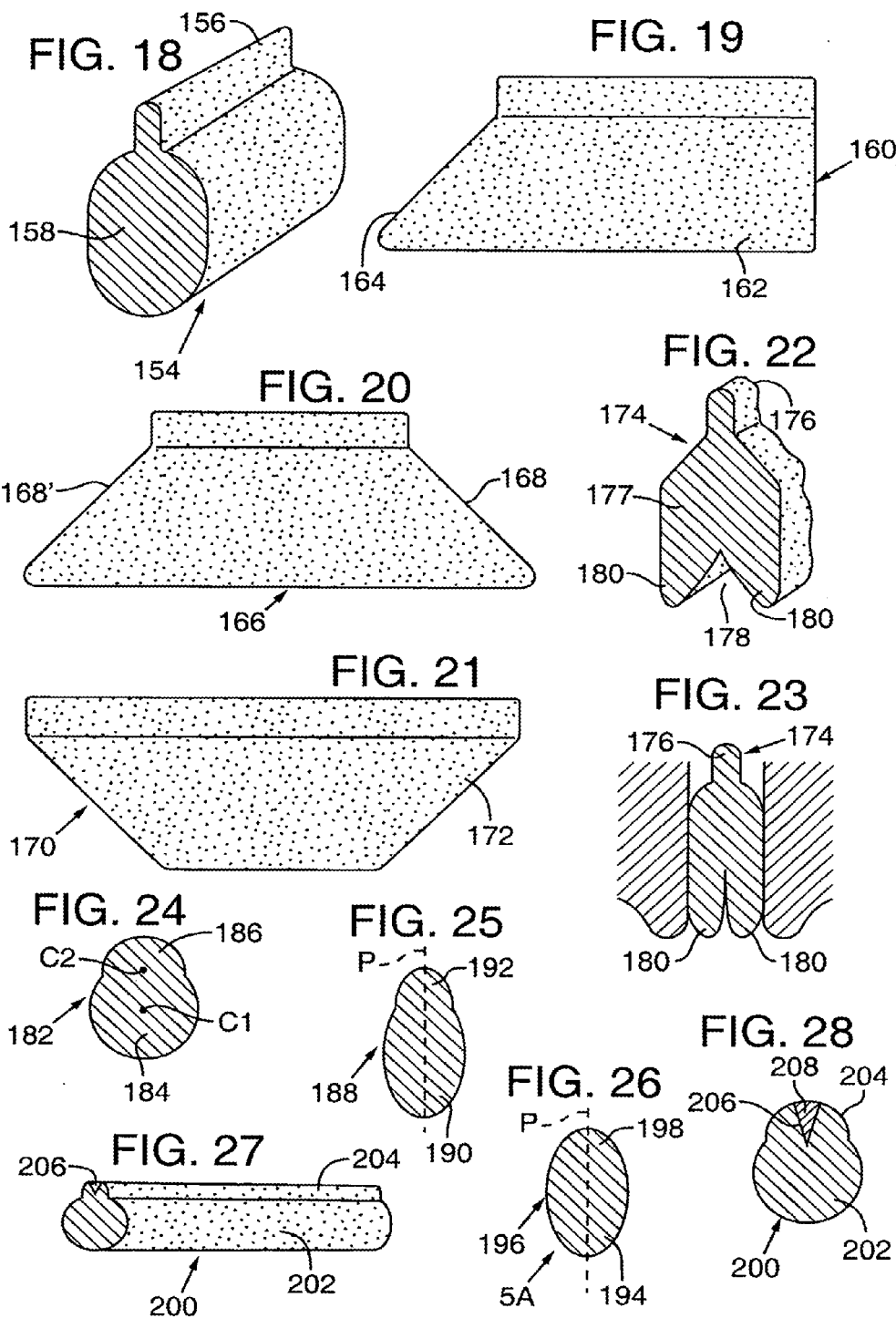

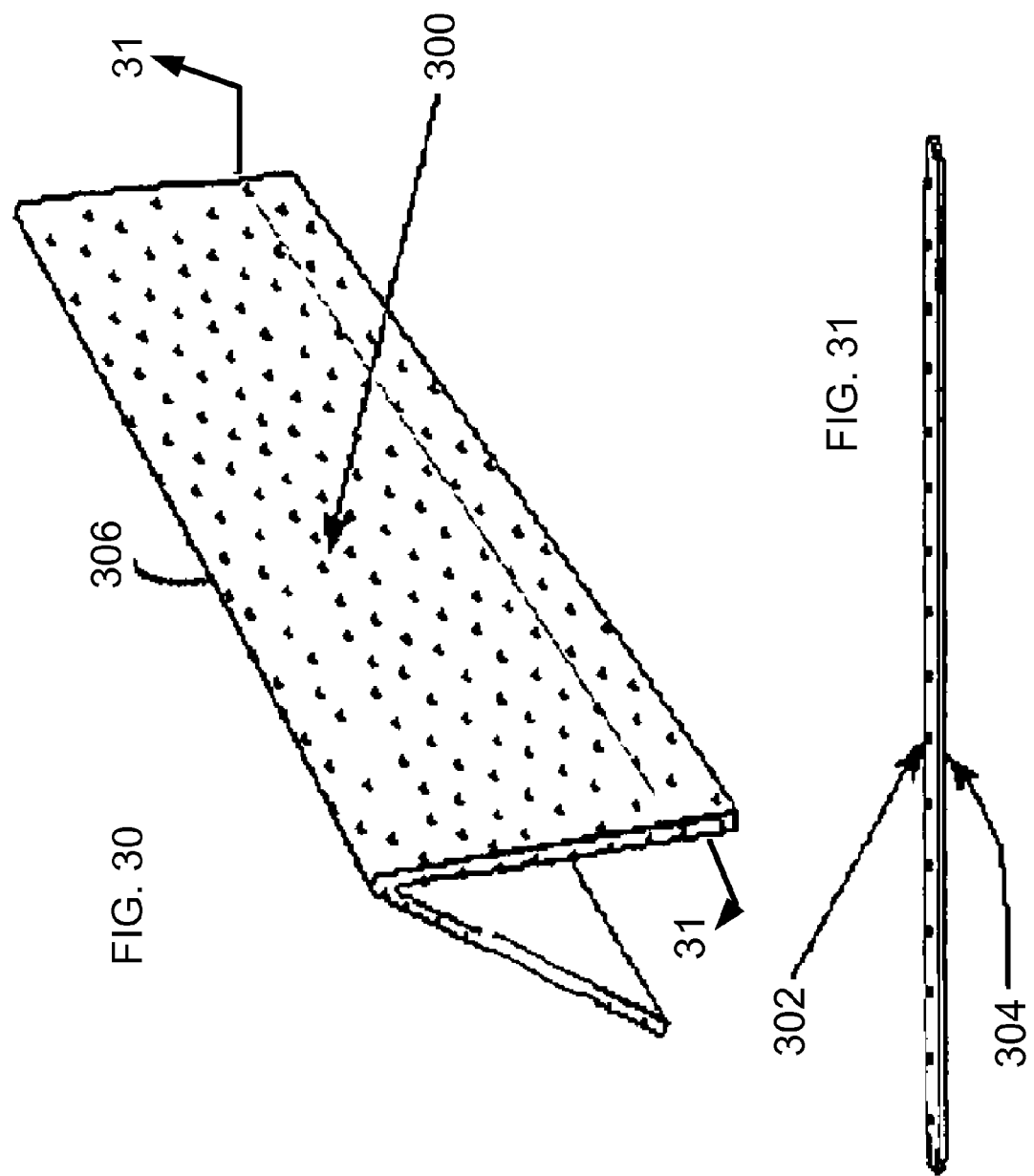

ANAL HYGIENIC PAD AND METHOD OF USE

CROSS-REFERENCE TO RELATED APPLICATION

This application is a continuation of U.S. patent application Ser. No. 10/781,043, filed on Feb. 17, 2004 now abandoned, which is incorporated herein by reference in its entirety.

FIELD OF THE INVENTION

This invention relates to the field of anal incontinence, more specifically to a device for absorbing anal leakage or other discharges.

BACKGROUND OF THE INVENTION

Hemorrhoids are varicosities of anal veins which are common following pregnancy, as one ages, or as a result of a more sedentary lifestyle. Those suffering from hemorrhoids are often not able to use common suppositories or crèmes for the relief of itching or pain during the day, because suppositories or crèmes can leak during ambulation or when it is not possible to remain supine. Hemorrhoids can also bleed or result in a mucus discharge that can stain clothing. Although any resulting anal discharge (which may include feculent material) may be in small amounts, it can be hygienically and emotionally distressing.

Anal incontinence (the loss of feces and contaminated moisture) or loss of blood from hemorrhoids or anal fissures, are common problems, particularly with activities such as jumping or running. Fecal incontinence can result from disease, such as nerve compression, impairment or degeneration; iatrogenic causes such as radical surgery in the lower spine or rectal zone of the body; spinal cord injuries; or advancing age.

The loss of even small amounts of discharge from the anus may give rise to a pungent and abhorrent odor, accompanied by a feeling of wetness and/or irritation. Anal incontinence may lead to the development of other diseases due to the bacteria laden moist environment created by this leakage.

Other exudations that may be encountered include anal secretions, such as secretions derived from Skene's and Bartholin's glands, sweat glands, and the like. Such secretions and exudations may mix to produce disagreeable odors, and may be accompanied by an uncomfortable feeling of wetness. This phenomenon becomes more pronounced in the case of a person having a discharge due to infection or venereal disease, or postoperative, post-delivery or hemorrhoidal inflammation.

Many people who suffer from anal incontinence wear large diapers and/or plastic or rubber undergarments such as are disclosed in U.S. Pat. No. 5,699,902. In addition, hygienic articles have been developed which are inserted into and retained within the anal sphincter to absorb rectal secretions (e.g. U.S. Pat. No. 4,804,380), or which are fixed to the natal cleft by an adhesive (e.g. U.S. Pat. No. 5,695,484). However, there remains a need for a comfortable, non-intrusive device, for those who suffer from anal incontinence, that can absorb anal or peri-anal secretions.

SUMMARY OF THE INVENTION

An absorbent pad has been designed which can be located external to the anal orifice to collect any anal discharge. The pad can be retained in the intergluteal space, between the buttocks, without the use of a supporting garment or adhesive. In particular embodiments, the pad is positioned external to the external anal sphincter, so that it is not retained by insertion in the anus.

The pad is used in a method of absorbing anal leakage in a subject by positioning the absorbent pad between the buttocks, external to the subject's anal orifice, such that the pad is retained between and by the buttocks. In this position, any anal or peri-anal discharge is absorbed by the pad. In particular embodiments of this method, the pad is devoid of corners and flat surfaces intermediate its ends, and the pad has a minor portion superimposed on a major portion. The minor portion of the pad has a cross-sectional area or width that is smaller than a cross-sectional area or width of the major portion, and both the minor and the major portions are curvilinear or partially cylindrical in cross-section. The reduced width minor portion facilitates insertion of the pad between the subject's buttocks, separation of the buttocks, and placement of the smaller portion adjacent the anal orifice. The larger major portion is not as close to the sensitive anal orifice, which avoids discomfort caused by the pressure exerted by the larger portion. However the larger portion is more readily frictionally retained between the buttocks, in the intergluteal space, without external attachment devices such as adhesive. In particular embodiments, a method is disclosed for treating hemorrhoids by inserting the pad between the buttocks, against the external anal orifice.

In some embodiments, the method delivers therapeutic substances (such as antibiotics, topical anesthetics or topical vasoconstrictors), for example in the treatment of hemorrhoids. The method includes positioning the intergluteal pad such that the pad is retained between the buttocks external to the subject's anus. The anterior portion of the pad is designed for insertion of the pad between the subject's buttocks in the anatomic intergluteal space adjacent to the anus, and the posterior portion is retained between the buttocks without the need for adhesive or other attachment devices. Insertion and retention of the pad adjacent to the anus alleviates one or more symptom of the hemorrhoids, or delivers drugs to the anal orifice.

The pad can be any of a variety of shapes, and particularly shapes which taper toward an anterior or leading edge of the pad. The anterior edge is usually sufficiently wide to be retained outside the anal orifice, but can be sufficiently narrow to extend at least partially within the anus (for example external to the anal valve). The pad is ideally substantially or completely retained exterior to the anus, with the posterior edge impinging against the surrounding buttocks to retain the pad in place. The pad can be symmetric or asymmetric, rounded or elongated, tapering or non-tapering. However particular embodiments taper from a relatively larger posterior portion to a relatively smaller anterior portion. The enlarged posterior portion is ideally large enough to at least slightly deform the surrounding buttocks to improve frictional engagement between the buttocks and the pad. The relatively small anterior portion is closer to the width of the anal orifice, and is more comfortably retained in the narrow intergluteal space adjacent the anus. The pads with a bipartite structure (with a major and minor portion) further enhance the comfort and retention of the pad.

BRIEF DESCRIPTION OF THE DRAWINGS

FIG. 4 is a cross sectional fragmentary view of an intergluteal absorbent pad of the invention.

FIGS. 5-9 are views similar to FIG. 4, but showing different embodiments of the pad which have a substantially quadrilateral shape.

FIGS. 10 and 11 are cross sectional views of the major portion of the pad, showing the major portion to be either arcuate (FIG. 10) or tapered (FIG. 11).

FIG. 12 is a cross sectional view of an intergluteal absorbent pad that does not have a major portion and a minor portion, but which has the side surfaces of the pad sloping toward a leading edge of the pad.

FIGS. 13-15 are cross-sectional fragmentary views showing pads which have major portions that are polygonal in shape.

FIG. 16 is a cross sectional view of an elongated intergluteal absorbent pad with a major portion and a minor portion, both of which taper symmetrically in a longitudinal direction.

FIG. 17 is a view similar to FIG. 16, but showing the major and minor portions of the pad tapering longitudinally in different directions.

FIG. 18 is a perspective view of an elongated intergluteal absorbent pad that has a fixed diameter along the length of the pad.

FIGS. 19-21 are side views of intergluteal absorbent pads similar to the pad shown in FIG. 18, but with one or two sloping end edges.

FIG. 22 is a cross sectional view of an intergluteal absorbent pad wherein the posterior portion of the pad is formed with a longitudinal groove.

FIG. 23 is a cross sectional view of the intergluteal absorbent pad of FIG. 22 disposed between the buttocks in the intergluteal space.

FIG. 24 is a cross sectional view of a unitary, one-piece yet bipartite intergluteal absorbent pad in which each portion of the pad has a cross section of a portion of a circle, each circle having different radii of curvature.

FIG. 25 is a cross sectional view of a bipartite pad in which each portion of the pad has a cross section of a partial ellipse. The pads may be either symmetric or asymmetric. In the symmetric embodiment, the major and minor portions may have the shape of partial spheres or ellipsoids.

FIG. 26 is a cross sectional view of an additional embodiment of a one-piece intergluteal pad with an elliptical cross section, and no minor and major portions.

FIG. 27 is an end perspective view of an elongated pad with a minor and a major portion that extends along its length, and a groove in the minor portion from which drugs or other agents can be released by compression of the pad in use.

FIG. 28 is an end view of the pad of FIG. 27.

FIG. 30 is a perspective view of another embodiment of a folded pad for placement in the gluteal fold.

FIG. 31 is a view taken along lines 30-30 of FIG. 30.

DESCRIPTION OF MULTIPLE SPECIFIC EMBODIMENTS

Figure 2:
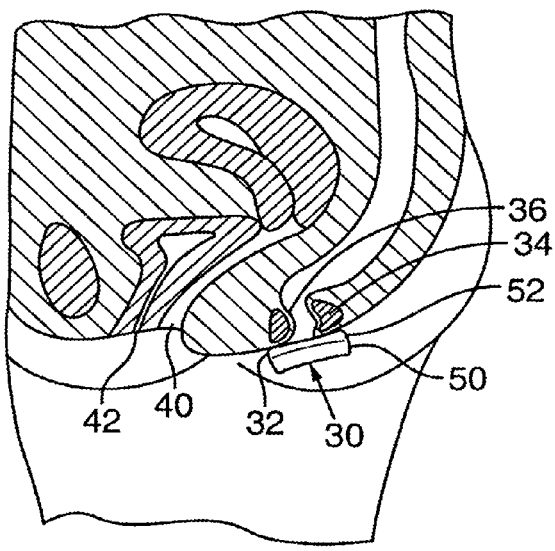
FIG. 2 is a cross-sectional sagittal view taken along line 2-2 of FIG. 1, showing a pad positioned adjacent the anal orifice.

The following definitions and methods are provided to better define the present invention and to guide those of ordinary skill in the art in the practice of the invention. As used herein and in the appended claims, the singular forms "a", "an", and "the" include plural referents unless the context clearly dictates otherwise. Thus, for example, reference to "a discharge" includes a plurality of such discharges and reference to "the absorbent material" includes reference to one or more materials and equivalents thereof known to those skilled in the art, and so forth.

Unless defined otherwise, all technical and scientific terms used herein have the same meaning as commonly understood to one of ordinary skill in the art to which this invention belongs.

DEFINITIONS

Absorbent: A material with sufficient absorbency to absorb and retain exudates discharged from a subject. Absorbency is dependent partially on the physical volume of the device. For example, a material is absorbent if it absorbs at least 3 ml of 0.9% saline, however an absorbent material may have a capacity of 20 grams or more.

Anal Leakage: Discharge from the anus, including involuntary discharges. Anal leakage can be fecal material, blood or secretions, or leakage of a medicinal agent placed into the anal canal, such as when a suppository is inserted rectally.

Anal sphincter: A circular layer of muscle in the anal canal. The circular coat is thickened at the upper end of the anal canal and forms the involuntary internal sphincter. The internal sphincter is surrounded by a sheath of striated muscle that forms the voluntary external sphincter. At the junction of the rectum and anal canal the blending of the internal sphincter with the deep part of the external sphincter and the puborectais muscles forms a distinct ring, called the anal rectal ring.

Anal Triangle: A region bounded behind by the tip of the coccyx, and on each side, by the ischial tuberosity and the sacrotuberous ligament, overlapped by the border of the gluteus maximus muscle. The anus lies in the midline, and on each side there is the ischiorectal fossia.

Anus or Anal Orifice: the lower opening of the anal canal. The anal canal is about 4 cm long and passes downward and backward from the rectal ampulla to the anus. Except during defecation, its lateral walls are kept in apposition by the levaotres ani muscles and the anal sphincters. The mucous membrane of the upper half of the anal canal is derived from endoderm, is sensitive to stretch, and is lined by vertical folds called anal columns which are joined together at their lower ends by semi-lunar folds called anal valves. The mucous membrane of the lower half of the anal canal (external to the anal valves) is derived from ectoderm, has no anal columns, and is extremely sensitive to pain.

Biodegradable material: A material having greater than or equal to about 70% biodegradation (percentage of theoretical carbon dioxide evolution) after 28 days when measured by a suitable test such as the Sturm test (Method 301B, Organization of Economic Cooperation and development).

Defecation: An act that results in the emptying of the descending colon, rectum, and anal canal by reflex acts and/or voluntary control of the anal sphincters.

Diagnostic test: Any procedure performed on a sample collected from a subject, wherein the procedure can be used to evaluate or monitor a disease or a disorder in the subject. A diagnostic test can be performed in a laboratory, a medical office or in the home environment.

Fecal incontinence: The involuntary discharge of fecal material from the anus.

Flushable: A product's capacity to pass through typical commercially available house toilets and plumbing drainage systems without causing clogging or similar problems that can be directly associated with the physical characteristics of the product.

Gluteal: The back of a hip that forms one of the fleshy parts where a human sits, it is also known as a buttock.

Gluteal Region: An anatomical region bounded superiorly by the iliac crest and inferiorly by the fold of the buttock. The region is largely made up of the gluteal muscles and a thick layer of superficial fascia.

Hemorrhoid: A mass of dilated veins in swollen tissue situated near the anal sphincter.

Intergluteal space: The space located between the right and left gluteals (buttocks), generally on a sagittal plane that includes the anus. The intergluteal space extends inferiorly toward the perineal body to the vaginal opening in the female (but does not include the vaginal opening), and toward the scrotum in the male (without including the scrotum).

The major portion of the pad is a larger portion, and a minor portion is a smaller portion. Large and small can be defined, for example, in terms of cross-sectional area, volume, or transverse dimension. In some embodiments, the pad is inserted between the gluteals with the minor portion as the leading edge inserted, in which example the minor portion would also be considered an anterior edge and the major portion would be a posterior portion.

Medicinal Agent: A therapeutic agent for treatment of the anal triangle. Specific, non-limiting examples of a medicinal agent are anesthetics, antibiotics, deodorants, or lubricants.

Natal cleft: The cleft formed where the external surfaces of the gluteals touch.

Occult blood: A diagnostic test performed to detect the presence of blood in a stool (fecal) sample. A test for occult blood is useful in the diagnosis of disease, such as colon cancer.

Supporting garment: A garment such as a belt or article of clothing, for example underwear, used to hold an absorbent pad in place on or in the body, for example in the anal triangle.

Vaginal orifice: The opening at the distal end of the vaginal canal.

Methods of Absorbing Leakage

Figure 1:
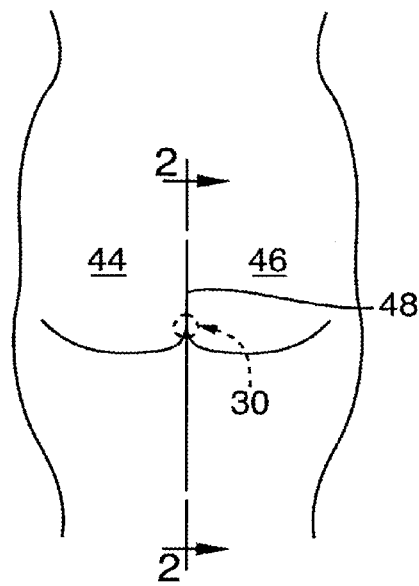
FIG. 1 is a schematic posterior view of the buttocks and thighs of a female subject in whom an absorbent pad has been positioned external to the anal orifice to collect discharge from the anus. The pad is shown retained in the intergluteal space, between the buttocks, without the use of a supporting garment or adhesive. The position of the pad is indicated by dashed lines.
Figure 3:
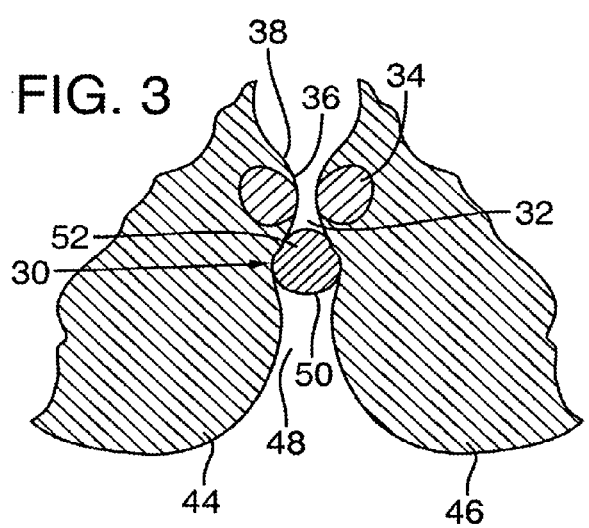
FIG. 3 is a horizontal sectional view of the anus and buttocks, showing the position of an anal pad external to the anal sphincter, with an enlarge posterior portion of the pad slightly deforming the buttocks to retain the pad in place.

Embodiment of FIGS. 1-3

A first embodiment of the invention is shown in FIGS. 1-3, in which an absorbent pad 30 is shown in place external to the anal orifice 32. The anal anatomy of a female is illustrated in these drawings, which show the anal sphincter 34 which closes the anal canal, and the anal valve 36 (FIG. 3) at the inferior aspect of the anal columns 38. The distal region of the anal canal, particularly inferior to the anal valve, is well innervated and exceedingly sensitive to pain, itching, and other disease processes. Anterior to the anal orifice 32 is the vaginal opening 40 and the urethral opening 42. The right and left gluteals 46, 48 appose one another, and generally form an intergluteal potential space 48 (FIGS. 1 and 3) that covers the anal orifice 32. This potential space can be opened by moving the gluteals away from one another (as particularly illustrated in FIG. 3).

Figure 3A:
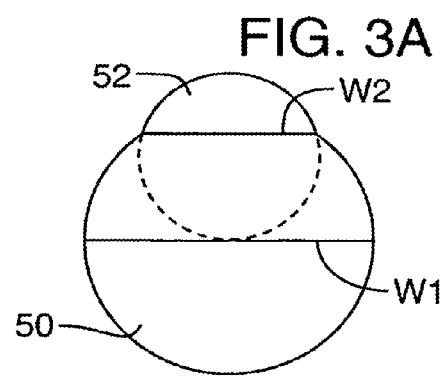

In the embodiment disclosed in FIGS. 1-3, the pad 30 is an elongated absorbent member, for example made of cotton, and having a bipartite profile with a major portion 50 and a minor portion 52. In the illustrated example, the major and minor portions each have a cross section that is a portion of a circle, where the portion of the circle of the major portion 50 has a greater diameter than the portion of the circle of the minor portion 52. The curvature of the minor portion is greater than the curvature of the major portion. The overall shape of pad 30 therefore includes a rounded major portion and a rounded minor portion, in which the transverse diameter or width W1 (FIG. 3A) of the major portion is greater than the transverse diameter or width W2 of the minor portion, so that the width of pad 30 tapers in the direction of minor portion 52. The width of major portion 50 is ideally greater than a diameter of an average anal orifice 32 (for example as determined by population studies), and minor portion 52 has a reduced width (and increased taper) to minimize pressure and discomfort in the area of anal orifice 32. The minimum width of minor portion 52 is, in some embodiments, substantially the same or slightly less than the maximum diameter of anal orifice 32. The outer profile of both the major and minor portions is arcuate to help conform to surrounding body tissues. The cross-sectional area of minor portion 52 in some embodiments is less than 50% of the cross-sectional area of pad 30, and has a cross-sectional area that is, for example, 10 to 49% of the total cross-sectional area of pad 30.

The reduced width of minor portion 52 is also advantageous for the insertion and retention of pad 30 in use. Gluteals 44, 46 are spread apart either by moving them apart, or by introducing the reduced width minor portion 52 as a leading edge of the pad between them, and advancing the pad toward anal orifice 32. As pad 30 is inserted into intergluteal space 48, the leading minor portion 52 gradually moves gluteals 44, 46 apart (FIG. 3), to facilitate acceptance of major portion 50. Once minor portion 52 is in place against anal orifice 32, major portion 50 provides an enlarged retention member that frictionally engages surrounding portions of gluteals 44, 46 to retain pad 30 in position. In this position, pad 30 is able to absorb leakage or other discharges (such as feces or even flatulence) from the anal orifice. The anal pad 30 is retained by the buttocks, in the intergluteal space, and does not extend beyond the natal cleft 32.

The pad is easily inserted between the buttocks and is easily retained in the intergluteal space without the need for auxiliary retaining means. Thus, a light pressure on the major portion 50 will cause the smaller minor portion 52 to open the buttocks slightly and allow pad 34 to take its proper position in the intergluteal space overlying the anal orifice 36. The radii of the respective portions is such that the anal orifice 36 is completely covered by the pad. The elongated pad extends along the intergluteal space 48, such that the length of the pad helps frictionally engage the pad in place, and resist dislodgement.

In particular embodiments, the intergluteal absorbent pad is formed of a soft absorptive material such as cellulose, cotton, or another suitable natural or synthetic fiber or sheeting. In one embodiment the pad is flushable, and can be made of biodegradable material. The pad may be made as described in U.S. Pat. No. 5,575,047, herein incorporated by reference.

Examples of Alternative Embodiments of Pads

Some other examples of alternative embodiments of the pad with a tapering portion are shown in FIGS. 4-28. Many of these embodiments are shown in cross-section as relatively flat, although they can be elongated (as indicated by the fragmentary depiction in each Figure).

In the embodiment shown in FIG. 4, a one piece absorptive pad 58 has a "tear-drop" or ovoid cross sectional shape which tapers progressively to a leading anterior edge portion 60 of limited transverse dimension from a posterior portion 62 of relatively large transverse dimension.

The pad 58 may be elongated transverse to the illustrated cross-section, or it may not be elongated (such that the length of the pad transverse to the cross section is less than the anterior-posterior dimension A-P of the cross-section). In elongated embodiments, the pad may be of uniform cross section along the length thereof, or may be tapered from one end to the other end thereof, and in particular embodiments is tapered in its anterior-posterior dimension AP. The user may readily and quickly insert the pad 58 into the intergluteal space by introducing leading anterior portion 60 into the inter-gluteal space. The pad is firmly self retained in the space and exhibits substantial absorptive capacity for discharges, and resists accidental dislodgement from the intergluteal space.

Other embodiments of the pad are shown which have posterior major portions of a polygonal (for example quadrilateral) shape, such as rectangular or square. Thus, as shown in FIG. 5, pad 62 includes a posterior portion 64 having flat bottom and side surfaces; and the anterior minor portion 66 has surfaces 68 which incline toward one another toward a leading edge 70. Anterior portion 66 therefore forms a wedge that parts the gluteals as it is introduced between them.

FIG. 6 shows a pad 72 that includes a posterior portion 74 of substantially square cross section; and a fingerlike anterior portion 76 of limited transverse dimension, which is much narrower than the corresponding transverse dimension of posterior portion 74. The juncture 78 of portions 74, 76 forms an essentially flat shoulder that extends transverse to the anterior-posterior dimension AP. In the disclosed embodiment, the anterior-posterior dimension of anterior portion 76 is substantially the same as the anterior-posterior dimension of posterior portion 74.

FIG. 7 shows a pad 80 that is similar to that of FIG. 8, except that the sides of anterior portion 84 diverge away from top edge 86, to present a more tapered profile. FIG. 8 shows a pad 88 having a posterior portion 90 and an anterior portion 92, wherein both portions are substantially quadrilateral in shape, except for a sloping flat shoulder 94 at the juncture of portions 90, 92. FIG. 9 shows a pad 95 that includes a posterior portion 96 of quadrilateral shape and an anterior portion 98 having upwardly converging side surfaces 100 and a flat leading edge 102.

While the pads shown in FIGS. 5-9 have posterior portions with flat bottom surfaces, the bottom surfaces may have other configurations. Thus, as shown in FIG. 10, the posterior portion P has an arcuate bottom surface A, while in FIG. 11, the posterior portion P' has converging surfaces C and an arcuate bottom edge B.

Further, alternative embodiments are shown in FIGS. 12 and 13. Thus, in FIG. 12, the non-bipartite pad 104 is of generally triangular cross section, with a posterior portion 106 of large cross section and an anterior portion 108 of small cross section. The pad 104 has flat, converging surfaces 110, a slightly curved bottom surface 112, rounded bottom edges 114 and a rounded leading edge 116. The pad 118 shown in FIG. 10 is similar to pad 106, except that the anterior portion 120 is transversely constricted and provides a linear juncture J between posterior portion 122 and anterior portion 120. This is an example of a bipartite pad that has major and minor portions.

FIG. 14 shows pad 124 which includes a posterior portion 126 of substantially hexagonal cross section and a transversely constricted anterior portion 128 with a rounded leading edge 130. The surfaces of posterior portion 126 are flat and edges thereof may be rounded.

FIG. 15 shows pad 132 which includes a posterior major portion 134 defined by opposed convergent flat surfaces 136 and a slightly rounded bottom surface 138; while anterior minor portion 140 is of a triangular cross section.

The pads may be suitably tapered in a longitudinal direction transverse to the AP direction. Thus pad 142, as shown in FIG. 16, has its anterior portion 144 and posterior portion 146 tapered in respect of both the longitudinal and transverse axes thereof; whereas in pad 148, as shown in FIG. 17, anterior portion 150 and posterior portion 152 are tapered longitudinally only.

FIG. 18 shows yet another embodiment of the pad 154, in which the anterior portion 156 and posterior portion 158 are substantially ovoid in cross-section, with the transverse width of anterior portion 156 much less than the transverse width of posterior portion 158.

The pads may be further modified, as shown in FIGS. 19-21. Thus, as shown in FIG. 19, the pad 160 has its posterior portion 162 sloped at one end as at 164, to make the pad conform to the anatomy of the user. Alternatively, as shown in FIG. 20, the pad 166 may be sloped at both opposite ends 168, 168'. Alternatively, as shown in FIG. 21, pad 170 has its posterior portion 172 sloped at opposite ends in a convergent configuration. If desired, in the foregoing embodiments, the anterior portions of the pads may also be sloped to converge toward one another.

FIG. 22 shows an embodiment of a pad 174 that has an anterior portion 176 and posterior portion 177. The posterior portion 177 is formed with a longitudinal groove 178 of normally triangular section, forming wings 180. When the pad 174 is inserted into the intergluteal space, as shown in FIG. 23, the wings 180 are resiliently urged toward each other and bear against the walls of the intergluteal space, adjacent to the buttocks, thereby increasing the retention of the pad within the intergluteal space.

The various forms of pads set forth above may also include the groove in the anterior portions thereof The pads set forth above which have opposed flat surfaces (e.g. FIGS. 6-9), are particularly adapted to conform to the walls defining the intergluteal space, and optimize the retention and absorption factors of the pads. Moreover, the grooves can be filled with therapeutic or other substances, so that the pad becomes a delivery vehicle.

Although some of the pads have been shown to taper longitudinally from one end to the other end, they may also taper from a central portion to the opposite ends thereof Thus, while the pad may be of uniform cross section throughout its length, it may also have a tapered form. No string or other removal aid is required, and the pad can be removed manually, such as with a gentle tap, or removed by normal use of the toilet (for example by defecation).

Another embodiment of the intergluteal absorbent pad 182 is shown in FIG. 24, in which the intergluteal absorbent pad 182 has a posterior portion 184 and anterior portion 186, each having a cross section that defines a portion of a circle. Each of the posterior and anterior portions is a portion of a sphere that is symmetric in all directions with respect to a center point, and has a constant radius. For example, posterior portion 184 is symmetric with respect to center C1, while anterior portion 186 is symmetric with respect to center C2.

FIG. 25 shows yet another embodiment of a pad 188 having merged portions 190, 192 which are of part elliptical cross section; the portion 190 having major and minor axes somewhat larger then those of portion 192, which also lends itself to easy insertion and removal. Portion 190 is symmetric in all directions with respect to perpendicular planes of symmetry, one of which is shown as P in FIG. 25. In this embodiment, the pad is not elongated in any direction, although in other embodiments longitudinal elongation is possible.

The pad 194, shown in FIG. 26, is of an elliptical cross section. This embodiment lacks a major portion and a minor portion, and instead has a cross-section that is completely symmetric with respect to an anterior-posterior plane AP. In use, pad 194 is inserted along the AP axis into the intergluteal space (either narrowed end of the pad can be the leading edge of insertion).

The pad 190 shown in FIG. 27 is an elongated version of the pad in FIG. 24 which has a more spherical configuration. Pad 190 in FIG. 27 is initially of a round cross section, but is formed into a larger and smaller portion by using a mechanical binding agent, such as thread or heat welding, similar to that described in Gerstenburger (U.S. Pat. No. 5,575,047). Alternatively, it can be sewn along the junction between the two portions with biodegradable thread, so that the pad is completely biodegradable, and can be flushed down a toilet. Biodegradable pads can be made by any method, such as those disclosed in U.S. Pat. No. 5,575,047, which is incorporated herein by reference.

The absorbent pads used to absorb anal discharge may be impregnated with selected scents, medications, or combinations thereof to mask the odor of the absorbed discharges, thereby providing a soothing and pleasant odor, and/or to provide appropriate treatment to external hemorrhoids, active anal fissures, traumatic, infectious or neoplastic lesions, or many other pathologies and conditions. In one embodiment, the pad includes activated charcoal, which may be used to absorb odors, such as those associated with flatulence. In another embodiment, the pad is impregnated in the posterior portion only. However, in other embodiments, the pad is impregnated in the anterior portion, or in both the anterior and posterior portions. In one embodiment, the pad includes a groove in the anterior or posterior portion, and the scent, medication, or another agent is added within the groove or impregnated in the pad adjacent to the groove.

FIG. 27 shows a cross-section of an embodiment of an elongated absorbent pad 200 that has been modified to carry and dispense lubricants alone or in admixture with deodorants, medications (such as a vasoconstrictor or anesthetic to treat hemorrhoids), and the like. The principles of the elongated embodiment could, however, be adapted to the non-elongated embodiments of the type shown in FIG. 24. In the embodiment shown in FIG. 27, intergluteal absorbent pad 200 includes posterior portion 202 and anterior portion 204, which is formed with a groove 206 extending longitudinally along the top of anterior pad portion 204. The groove is prefilled with a material 208, for example, with an ointment, lubricant or other carrier for admixed medications, deodorants and the like. Placing the intergluteal absorbent pad in the intergluteal space, with anterior portion 204 adjacent to the anal orifice, causes the normal transverse constriction of the pad 200 (and particularly compression of anterior portion 204) to dispense materials which have a suitable viscosity, to the areas surrounding the anal orifice.

It has been found that the curvilinear surface portions and the non-uniform cross sections of the several pads shown herein, is highly effective in positioning the pad between the buttocks and retaining it in place. Further, there is no tendency to force the buttocks apart or to exert undue pressure against their medial wall portions.

In one embodiment, the pads are molded or otherwise formed from the cellulose base material, to the desired cross sectional and longitudinal configurations by apparatus and procedures known in the art, or formed as described in Gerstenburger.

In an additional embodiment, the intergluteal absorbent pads are used to absorb discharge from the anus, and a diagnostic test is then performed on the absorbed discharge. In one embodiment, the discharge is fecal material. In another embodiment, the discharge is a bodily fluid, such as blood or a secretion, such as a secretion derived from Skene's or Bartholin's glands. In yet another embodiment, the discharge includes cells, such as cells of the anal or rectal epithelium, and the cells are analyzed using a diagnostic test. The diagnostic test can be performed directly on the discharge absorbed by the intergluteal absorbent pad, or the discharge or a component of the discharge can be extracted from the intergluteal pad prior to performing the diagnostic test (see U.S. Pat. No. 5,094,956).

The diagnostic test can detect the presence or absence of a cell type (e.g. see U.S. Pat. No. 5,124,252; U.S. Pat. No. 5,965,375), a protein (e.g. see U.S. Pat. No. 5,190,881; U.S. Pat. No. 5,661,010), or a nucleic acid (e.g. see U.S. Pat. No. 5,538,851; U.S. Pat. No. 5,459,034) in the anal discharge. The diagnostic test can also be used to detect occult blood (see U.S. Pat. No. 4,920,045; U.S. Pat. No. 5,563,071), or the presence of a virus, such as human papillomavirus (HPV), or a microorganism, such as an enteric pathogen (see U.S. Pat. No. 5,705,332; U.S. Pat. No. 5,627,275). The diagnostic test can be a qualitative, semi-quantitative, or quantitative test. In one specific, non-limiting example, the diagnostic test is used to detect a biological parameter associated with colorectal cancer or anal cancer.

In a specific, non-limiting example, anal discharge is collected on an absorbent anal pad and a diagnostic test is then performed on the anal discharge to detect human papillomavirus (HPV) infection. For example, the diagnostic test can detect the presence of HPV nucleic acid (see U.S. Pat. No. 5,580,907; U.S. Pat. No. 5,876,922; U.S. Pat. No. 5,783,412; U.S. Pat. No. 5,447,839; U.S. Pat. No. 5,283,171). Alternatively, the diagnostic test can detect the presence of a protein associated with HPV infection (see U.S. Pat. No. 5,045,447).

In one embodiment, a kit is provided for collecting a sample of anal discharge. The kit includes an absorbent pad, and a packaging means, such as a plastic vial or a plastic bag, for packaging the absorbent pad. The kit can also include directions for the use of the pad, and instructions for the use of the package for mailing the pad to a remote laboratory, where a diagnostic test (e.g. a test to detect the presence of HPV), is performed.

Figure 29:
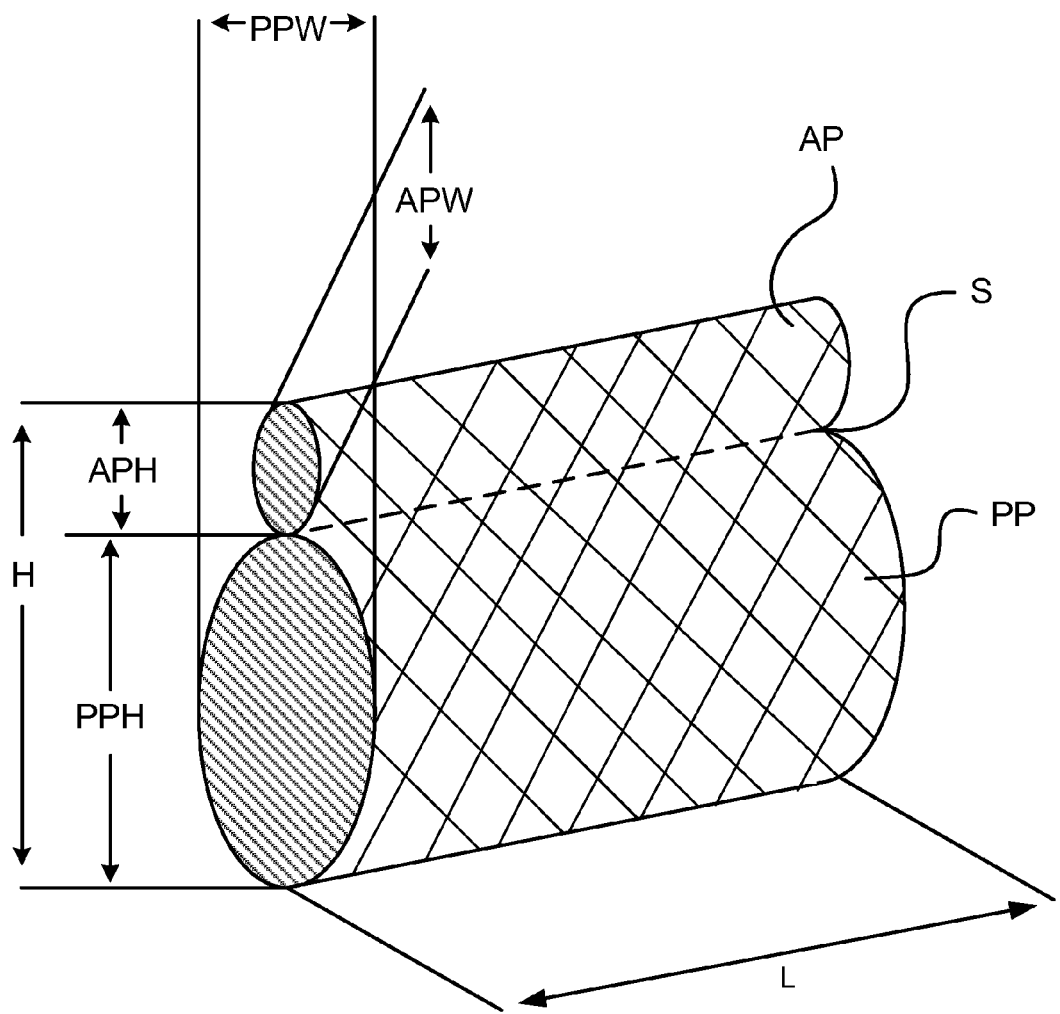
FIG. 29 is a perspective view of an elongated pad.

FIG. 29 shows a particular embodiment wherein the absorbent pad is formed of a polypropylene or polyester non-woven fabric with a rayon sliver core. The absorbent pad has an overall length L of about 15 to about 75 mm, and an overall height H of about 19 to about 22 mm. Of the overall height of the absorbent pad, the anterior portion AP of the absorbent pad has a height APH of about 4 to about 7 mm. The posterior portion PP of the absorbent pad has a height PPH of about 12 to about 18 mm. In addition, posterior portion PP of the pad has a width PPW of about 8 to about 10 mm. Anterior portion AP has a width APW less than width PPW of posterior portion PP of the pad. In one specific, non-limiting example, width PPW of posterior portion PP of the absorbent pad is from about 4 to about 7 mm. Posterior portion PP of the pad is demarcated from anterior portion AP of the pad by stitching S. In one specific, non-limiting example the stitching is standard 401 chain stitch of about 8-10 SPI.

FIGS. 30-31 show another embodiment of a rectangular pad 300 which includes an absorbent front 302 (FIG. 31) and a substantially liquid impermeable (such as a polypropylene) backing 304. Pad 300 is folded (as shown in FIG. 30) to present a tapered profile with a leading edge 306. In use, leading edge 306 of folded pad 300 is inserted in the intergluteal space, with edge 306 against the anus. The large surface area of the faces of pad 300 frictionally engage the surrounding tissue to hold the pad in place during ambulation and other activities. In a particularly disclosed embodiment, pad 300 has a length of at least 15 mm, for example 15-75 mm, and a width of at least 35 mm, for example 38-45 mm. An indentation or other indicia can be provided on the pad to indicate where it should be folded prior to insertion in the intergluteal space, or alternatively the pad can be provided in a pre-folded condition.

In view of the many possible embodiments to which the principles of the invention may be applied, it should be recognized that the illustrated embodiments are only particular examples of the invention and should not be taken as a limitation on the scope of the invention. Rather, the scope of the invention is defined by the following claims. We therefore claim as our invention all that comes within the scope and spirit of these claims.

I claim:

1. A method for absorbing leakage from an anus of a subject, comprising positioning a non-adhesive intergluteal absorbent pad external to the subject's anal orifice such that the pad is retained frictionally between the buttocks without an adhesive to attach the pad to the buttocks, so that discharge from the anus is absorbed by the absorbent material of the pad,
wherein the pad has a minor portion superimposed on a major portion, the minor portion having a cross-sectional area smaller than a cross-sectional are of the major portion and wherein the minor portion is tapered along its width to facilitate insertion between the subject's gluteals and retention in the intergluteal space, and a portion of the minor portion is positioned against the anus, and
wherein the minor portion has a length that is at least as long as the length of the major portion.

2. The method of claim 1, further comprising absorbing discharge from the anus in the absorbent material of the pad.

3. The method of claim 1, wherein the absorbent material is a highly absorbent non-swellable material.

4. The method of claim 1, wherein the pad has a uniform cross-section along its entire length or is tapered along its length.

5. The method of claim 1, wherein the minor and major portions of the pad have a elliptical cross-section with a major axis, wherein the major axis of the minor portion is less than the major axis of the major portion.

6. The method of claim 1, wherein the pad includes an agent for absorbing odors.

7. The method of claim 1, wherein the pad carries a therapeutically effective amount of a medicinal agent that is dispensed from the pad for anal delivery of the agent, and the subject is a subject in need of the medicinal agent.

8. The method of claim 7, wherein the medicinal agent is an anesthetic or a lubricant.

9. The method of claim 1 wherein the pad is placed between the buttocks of the subject and absorbs excess leakage from the anus, and wherein the leakage comprises fecal material, glandular secretions, and/or blood.

10. The method of claim 1, wherein the pad is placed between the buttocks of the subject and absorbs excess suppository leakage, flatulence, hemorrhoid bleeding, fissure bleeding, or fecal incontinence.

11. The method of claim 1, wherein the pad is placed external to the anal sphincter, against the anal orifice.

12. The method of claim 1, wherein the pad has a tapered leading edge that is inserted between the subject's buttocks to push the buttocks apart as the leading edge of the pad is inserted between the buttocks.

13. The method of claim 12, wherein the tapered leading edge is positioned against the anal orifice, and a remainder of the pad has a width which is wider than a normal anatomic intergluteal space, such that the remainder of the pad is frictionally engaged and retained by opposing gluteals.

14. The method of claim 13, wherein the pad is elongated and positioned adjacent and external to the anal orifice but not a vaginal orifice.

15. The method of claim 1, further comprising performing a diagnostic test on the discharge from the anus.

16. The method of claim 15, wherein the diagnostic test is an analysis of occult blood in a discharge including stool.

17. The method of claim 1, further comprising treating a symptom of a subject with hemorrhoids wherein the pad comprises a longitudinally extending major portion and a longitudinally extending minor portion integrated with the posterior portion, wherein the minor portion has a smaller transverse section diameter relative to the larger transverse section diameter of the major portion, wherein the minor portion is designed for insertion of the pad between the subject's buttocks in the anatomic intergluteal space adjacent to the anus, and the major portion is attached to the anterior portion such that is retained between the buttocks, wherein insertion and retention of the pad adjacent to the anus alleviates a symptom of the hemorrhoids.

18. The method of claim 1, wherein the discharge comprises flatulence or fecal matter, and the method further comprises absorbing flatulence or fecal matter in the pad.

19. The method of claim 18, wherein the pad comprises an odor absorbing material, and the pad neutralizes odor of the flatulence or fecal matter in the pad.

20. The method of claim 19, wherein the odor absorbing material comprises activated charcoal.

21. A method for absorbing leakage from a subject's anus, comprising inserting a non-adhesive pad into the subject's intergluteal space, positioning the pad adjacent to the subject's external anal orifice, and absorbing leakage from the subject's anus into the pad, wherein the pad is non-adhesive and is retained frictionally between the buttocks without an adhesive to attach the pad to the buttock, devoid of corners and flat surfaces intermediate its ends, and the pad has a minor portion superimposed on a major portion, the minor portion having a cross-sectional area smaller than a cross-sectional area of the major portion and a length greater than a length of the anal orifice, wherein both the minor and the major portion are curvilinear in cross-section, and wherein the minor portion facilitates insertion between the subject's buttocks and retention in the anal space without being inserted into the anal orifice.

22. The method of claim 21, wherein the pad includes an odor-absorbing agent.

23. The method of claim 21, wherein the pad is elongated and has a uniform cross-section along its entire length, or is tapered along its length.

24. The method of claim 23, wherein the pad is elongated, and, when placed in the intergluteal space, extends external to the anal orifice and a vaginal opening to absorb leakage from the vagina in addition to leakage from the anus.

25. The method of claim 21, wherein the pad carries a therapeutically effective amount of a medicinal agent, and positioning the pad comprises administering the medicinal agent to the subject.

26. The method of claim 25, wherein the medicinal agent is an anesthetic or a lubricant.

27. The method of claim 21, wherein the pad is placed between the buttocks of the subject to absorb excess leakage from the anus, and wherein the leakage comprises fecal material, anal glandular secretions, and/or anal blood.

28. The method of claim 21, wherein the pad is placed between the buttocks of the subject to absorb excess suppository leakage, flatulence, hemorrhoid bleeding, anal fissure bleeding, or fecal incontinence.

29. The method of claim 28, wherein the leakage comprises flatulence or fecal matter, and the method further comprises absorbing flatulence or fecal matter in the pad.

30. The method of claim 21, wherein the pad is placed external to the anal sphincter.

31. The method of claim 21, wherein the pad has a tapered leading edge that is inserted between the subject's buttocks to push the buttocks apart as the leading edge of the pad is inserted between the buttocks.

32. The method of claim 31, wherein the tapered leading edge is positioned against the anal orifice, and a remainder of the pad has a width which is wider than a normal anatomic intergluteal space, such that the remainder of the pad is frictionally engaged and retained by opposing gluteals.

33. The method of claim 21, further comprising performing a diagnostic test on the discharge from the anus.

34. The method of claim 33, wherein the diagnostic test is an analysis of occult blood in a discharge including stool.

35. A method for absorbing leakage from an anus of a subject, comprising positioning a non-adhesive intergluteal absorbent pad external to the subject's anal orifice such that the pad is frictionally retained between the buttocks without an adhesive attaching the pad to the buttocks, so that discharge from the anus is absorbed by the absorbent material of the pad, wherein the pad includes a cavity in which a medicinal agent is placed prior to positioning the pad, wherein the pad comprises a major portion and a minor portion, the minor portion is positioned adjacent the anal orifice and is at least the same length as the major portion, and the length of the minor portion is sized to restrict insertion of the pad into the anal orifice.

36. The method of claim 35, wherein the cavity is compressed between the buttocks when the pad is positioned.

37. The method of claim 36, wherein the cavity communicates with an exterior surface of the pad.

38. The method of claim 37, wherein the cavity is a recess in an exterior surface of the pad.

39. The method of claim 35, wherein the pad is elongated, and the cavity extends longitudinally along the pad.

* * * * *